United States Patent
Gocho

(10) Patent No.: US 7,353,692 B2
(45) Date of Patent: Apr. 8, 2008

(54) LEAKAGE TESTER

(75) Inventor: Masanori Gocho, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/369,569

(22) Filed: Mar. 7, 2006

(65) Prior Publication Data

US 2006/0196250 A1    Sep. 7, 2006

Related U.S. Application Data

(63) Continuation of application No. PCT/JP2004/013025, filed on Sep. 8, 2004.

(30) Foreign Application Priority Data

Sep. 12, 2003   (JP)   ............. 2003-322131

(51) Int. Cl.
  *G01M 3/04*   (2006.01)
  *G01M 3/34*   (2006.01)
(52) U.S. Cl. ............... 73/49.2; 73/49.3; 73/40
(58) Field of Classification Search ............ 73/40, 73/49.2, 49.3, 52, 37; 340/605
See application file for complete search history.

(56) References Cited

U.S. PATENT DOCUMENTS

| | | | | |
|---|---|---|---|---|
| 3,818,752 | A * | 6/1974 | Lindeberg | 73/49.2 |
| 6,412,334 | B1 * | 7/2002 | Kral et al. | 73/49.2 |
| 6,494,082 | B1 * | 12/2002 | Mizobe | 73/40 |
| 2002/0056452 | A1 * | 5/2002 | Brewer et al. | 128/202.22 |
| 2004/0139789 | A1 * | 7/2004 | Masters | 73/49.2 |
| 2005/0056081 | A1 * | 3/2005 | Gocho | 73/40 |

FOREIGN PATENT DOCUMENTS

| | | |
|---|---|---|
| JP | 58-144728 | 8/1983 |
| JP | 04-221733 | 8/1992 |
| JP | 05-220110 | 8/1993 |
| JP | 08-015079 | 1/1996 |
| JP | 10-243914 | 9/1998 |
| JP | 3186438 | 5/2001 |
| JP | 2001-170005 | 6/2001 |
| JP | 2001-264208 | 9/2001 |
| JP | 2003270077 A * | 9/2003 |
| WO | WO 03/078955 A1 | 9/2003 |

* cited by examiner

*Primary Examiner*—Hezron Williams
*Assistant Examiner*—Tamiko Bellamy
(74) *Attorney, Agent, or Firm*—Scully, Scott, Murphy & Presser, P.C.

(57) ABSTRACT

An inexpensive and compact leakage tester is provided, which performs a leakage determination on a measurement object automatically and with high accuracy. The leakage tester of the present invention includes; a pressurizing device for pressurizing the inside of a measurement object; a pressurizing controlling section for controlling the pressurizing device so as to perform a first pressurizing operation and a second pressurizing operation; a pressure detecting section for detecting a pressure value in the measurement object at the stoppage of the first pressurizing operation and a pressure change value in the measurement object after the stoppage of the second pressurizing operation; a volume estimating section for estimating a volume of the measurement object based on at least the pressure value; and a leak determination section for determining a leak state of the measurement object based on pressure change information and the pressure change value.

11 Claims, 7 Drawing Sheets

LEAKAGE TESTER

CROSS REFERENCE TO RELATED APPLICATION

This application is a continuation application of PCT/JP2004/013025 filed on Sep. 8, 2004 and claims benefit of Japanese Application No. 2003-322131 filed in Japan on Sep. 12, 2003, the entire contents of which are incorporated herein by this reference.

BACKGROUND OF THE INVENTION

1. Field of the Invention

The present invention relates to a leakage tester for detecting a leak in an airtight article, for example, an endoscope.

2. Description of the Related Art

For example, an endoscope is a reusable medical device and thus must always be washed and disinfected. In this regard, the presence of a pin hole or looseness of a connection in the endoscope causes the intrusion of a liquid such as water or disinfectant into the endoscope, which may cause a failure in an electric system such as an optical fiber or a CCD. Thus, in order to prevent such a situation, a leak test must be carried out on the endoscope.

A common leak test method for an airtight measurement object such as an endoscope includes immersing the measurement object into water, injecting pressurized air into the measurement object, and checking for the bubbles thus generated. However, this method requires a human operator to execute visual checks and thus fails to automate the leak test. As a result, a manual operation is constantly required.

In view of this, in order to automatically detect a leak in the measurement object, it is common to use a method of pressurizing the inner portion of the measurement object to seal the measurement object and detecting a variation in internal pressure to thereby determine whether or not there is leakage. Further, as an example of a high-accuracy automatic measurement method, Japanese Unexamined Patent Application Publication No. 4-221733 or Japanese Patent No. 3186438 discloses a technique of determining the presence/absence of leakage by detecting a pressure difference between the pressure of a gas inside the measurement object and the pressure of a pressurized gas supplied from a pressurized gas source by using a differential pressure sensor. Further, as an example of a simpler leak test method, Japanese Unexamined Patent Application Publication No. 5-220110 discloses a method of detecting the internal pressure of an endoscope using a gauge pressure sensor.

However, the problem with the above-described method using the differential pressure sensor as disclosed in Japanese Unexamined Patent Application Publication No. 4-221733 and Japanese Patent No. 3186438 is that, in addition to the high cost of the sensor, the method requires a complex wiring structure and also complex correction processing, which all add to the overall complexity of the system.

Further, the above-described method using a gauge sensor as disclosed in Japanese Unexamined Patent Application Publication No. 5-220110 requires a pressure sensor having a full scale for a pressure equal to or higher than that used for the pressurization, thus leading to a problem in that the measurement must be performed for a long period of time in order to ensure accuracy when the changes in pressure due to leakage are minute.

The present invention has been made in view of the above-mentioned problems and provides an inexpensive and compact leakage tester capable of determining a leak in a measurement object automatically and with accuracy.

SUMMARY OF THE INVENTION

A leakage tester according to the present invention includes: a pressurizing apparatus for pressurizing a measurement object by introducing gas into the measurement object; a pressurization control section for controlling the pressurizing operation by the pressurizing apparatus such that the pressuring apparatus performs a first pressurizing operation to stop pressurizing before reaching a predetermined pressure after starting pressurizing and a second pressurizing operation to stop pressurizing after pressurized until reaching the predetermined pressure after the first pressurizing operation; a pressure detecting section for detecting the pressure in the measurement object, the pressure detecting section detecting at least the pressure value in the measurement object when the first pressurizing operation is stopped and the value of pressure change in the measurement object after the second pressurizing operation is stopped; a volume estimating section for estimating the volume of the measurement object based on the pressurizing amount of the first pressurizing operation and the pressure value when the pressurizing operation is stopped; and a leak determination section for determining the leakage state of the measurement object based on the pressure change information obtained in accordance with the volume of the measurement object estimated by the volume estimating section and the amount of pressure change detected by the pressure detecting section after the second pressurizing operation is stopped.

DETAILED DESCRIPTION OF THE PREFERRED EMBODIMENT(S)

Hereinbelow, an embodiment of the present invention will be described with reference to the drawings.

Figure 1:
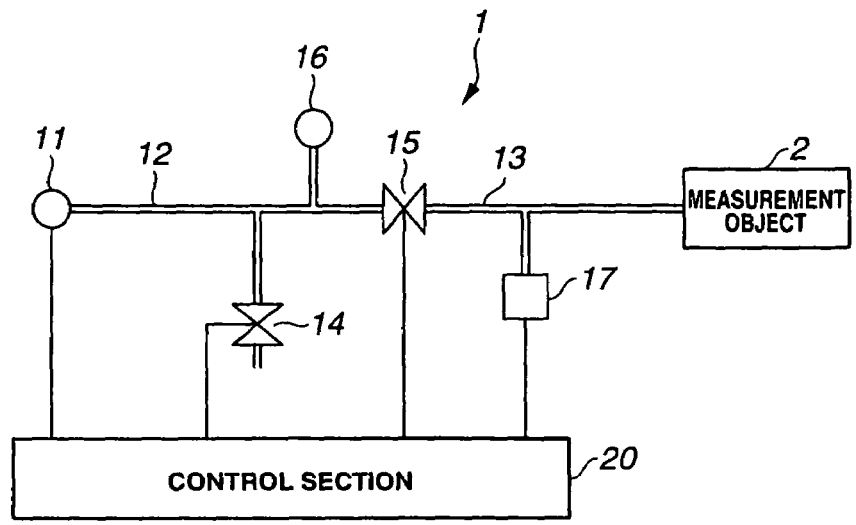
FIG. 1 is a block diagram showing the basic configuration of a leakage tester.
Figure 2:
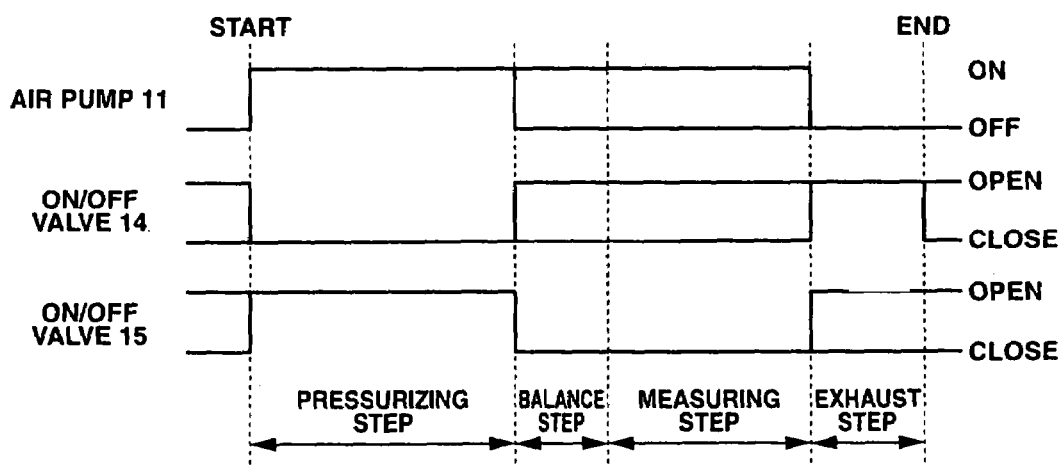
FIG. 2 is a time chart illustrating how an air pump and on/off valves operate throughout the entire process.
Figure 3:
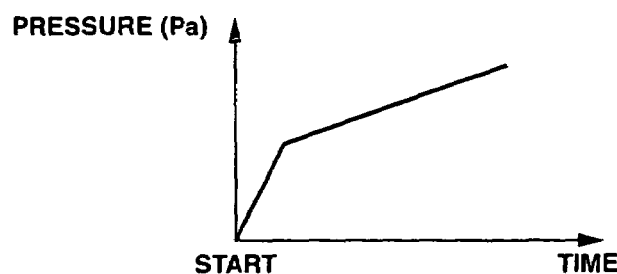
FIG. 3 is a diagram showing the transition of a pressure sensor output during the pressurization of an endoscope.
Figure 4:
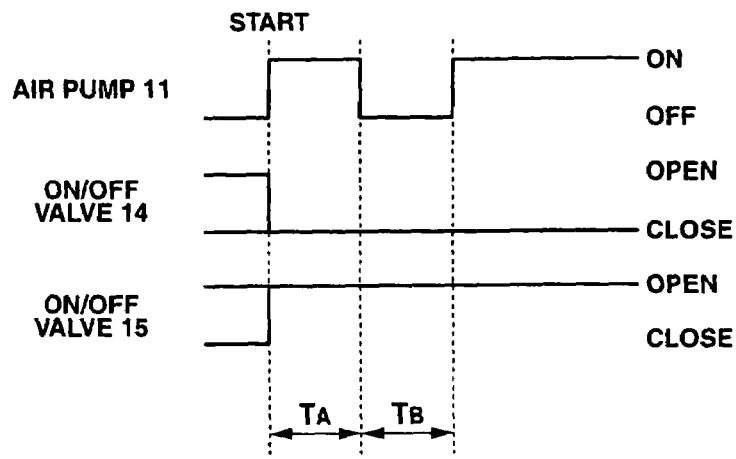
FIG. 4 is a time chart illustrating how the air pump and the on/off valves operate during a volume measurement in the case where a leakage on the leakage tester side can be ignored.
Figure 5:
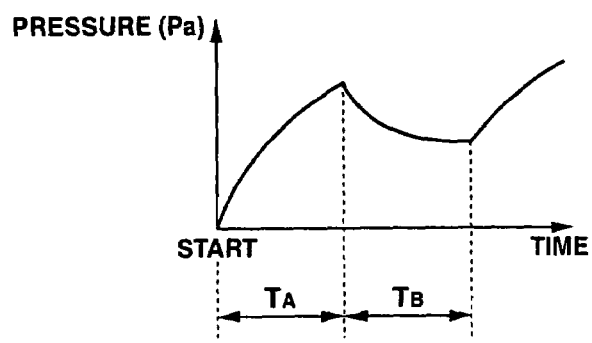
FIG. 5 is a diagram showing the transition of the pressure sensor output during the volume measurement.
Figure 6:
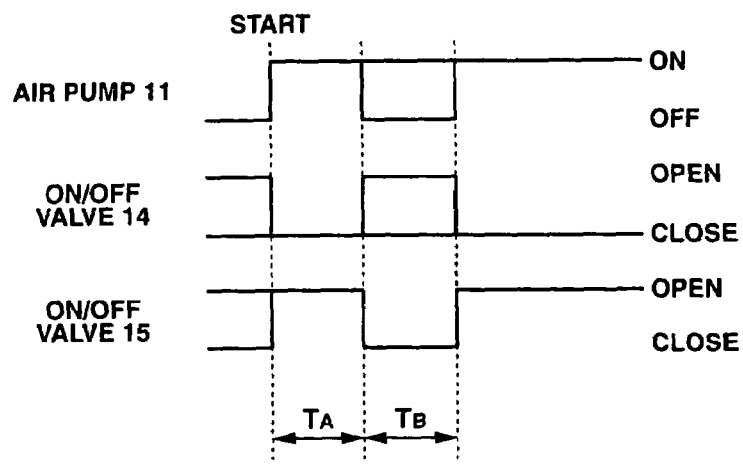
FIG. 6 is a time chart illustrating how the air pump and the on/off valves operate during the volume measurement in the case where the leakage on the leakage tester side cannot be ignored.
Figure 7:
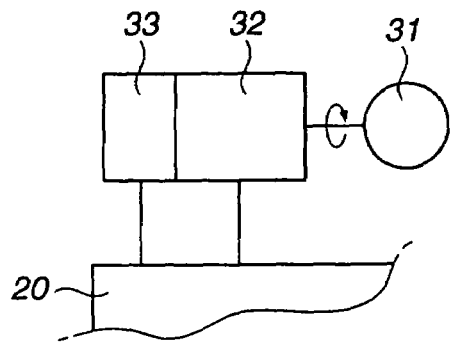
FIG. 7 is a diagram showing the general configuration of the air pump.
Figure 8:
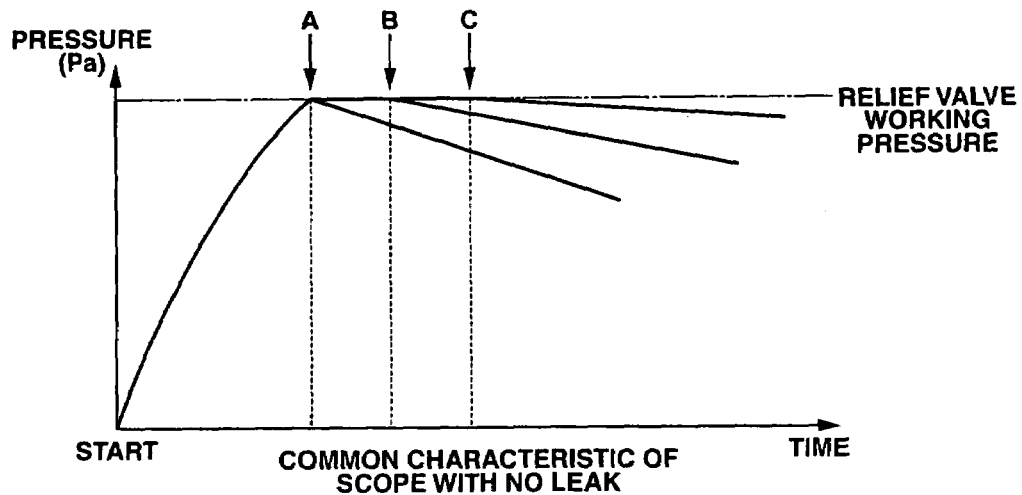
FIG. 8 is a diagram illustrating the transitions in pressure in an endoscope with no leak according to differences in pressurization time.
Figure 9:
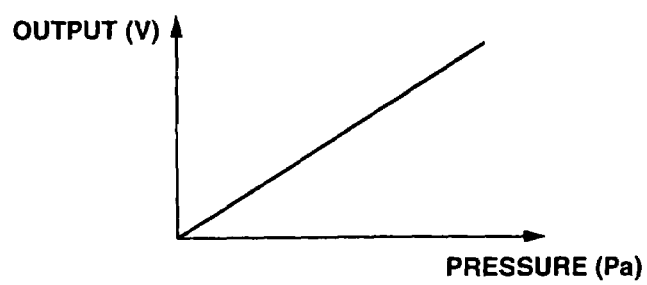
FIG. 9 is a diagram illustrating an input/output characteristic of a common gauge pressure sensor.
Figure 10:
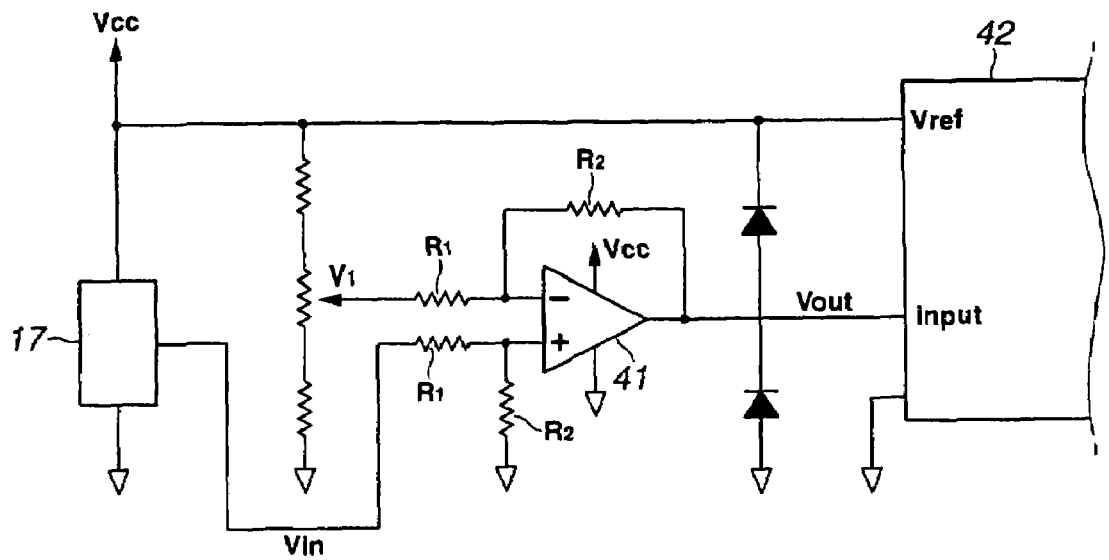
FIG. 10 is a conceptual diagram of a signal amplifier circuit.
Figure 11:
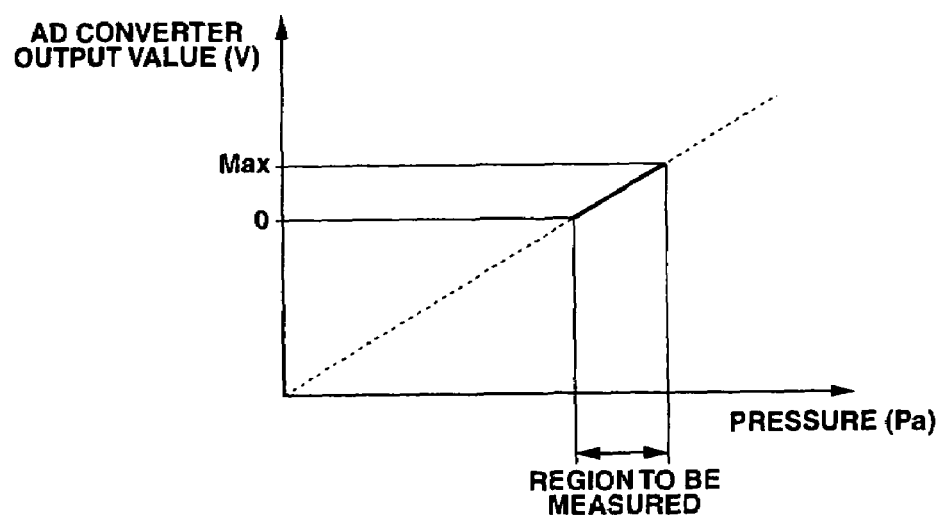
FIG. 11 is a diagram illustrating a method of performing signal amplification in a region that is subject to signal amplification.
Figure 12:
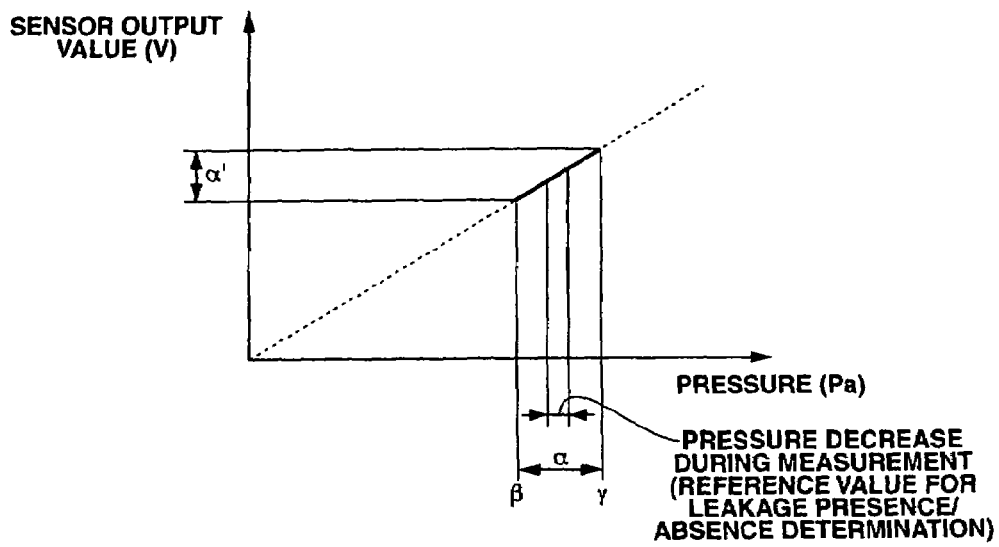
FIG. 12 is a diagram showing how V1, R1, and R2 are determined in FIG. 10.
Figure 13:
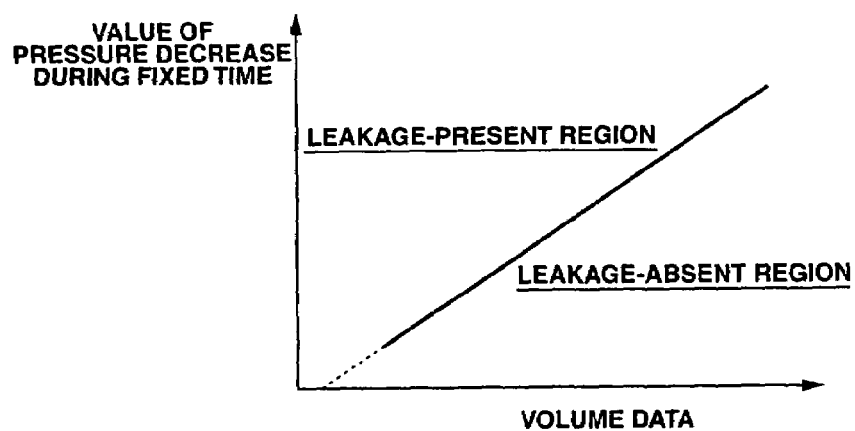
FIG. 13 is a diagram illustrating an example of regions for leakage presence/absence determination.
Figure 14:
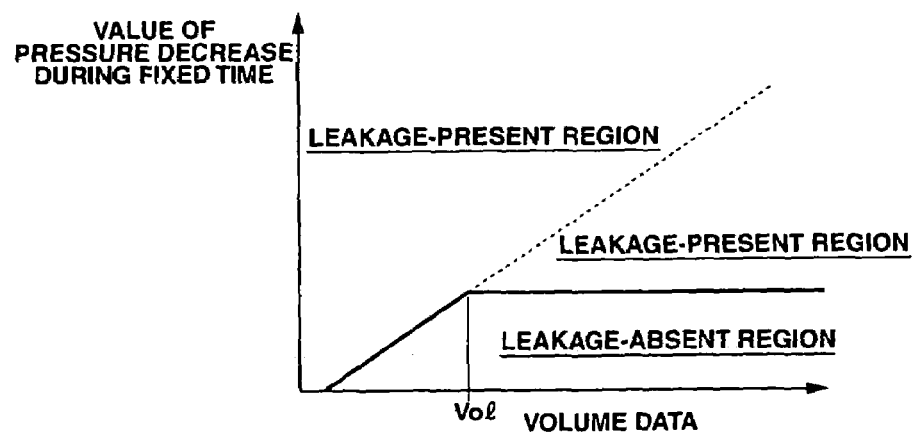
FIG. 14 is a diagram illustrating an example of regions for leakage presence/absence determination which is different from that of FIG. 13.
Figure 15:
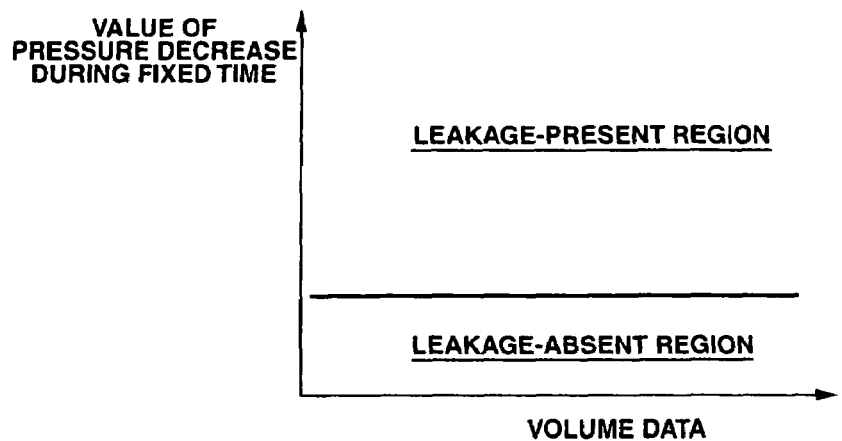
FIG. 15 is a diagram illustrating an example of regions for leakage presence/absence determination which is different from those of FIGS. 13, 14.
Figure 16:
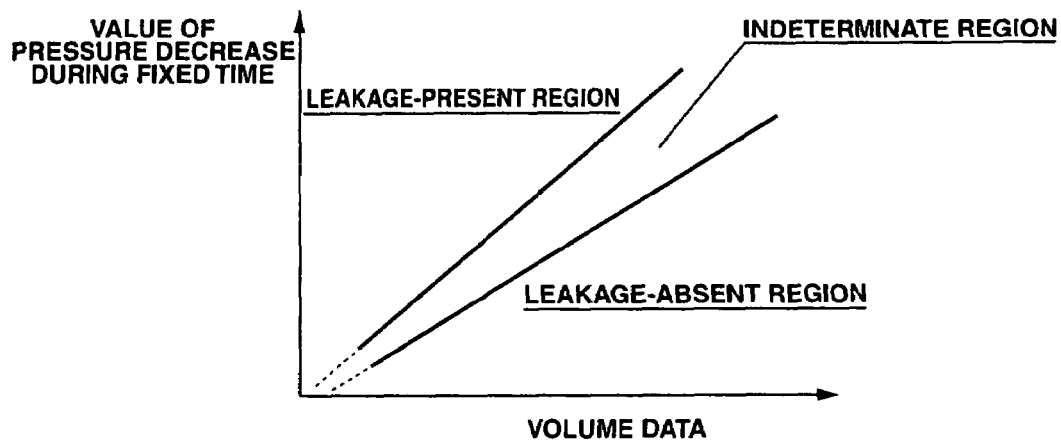
FIG. 16 is a diagram illustrating an example of regions for leakage presence/absence determination which is different from those of FIGS. 13, 14, 15.
Figure 17:
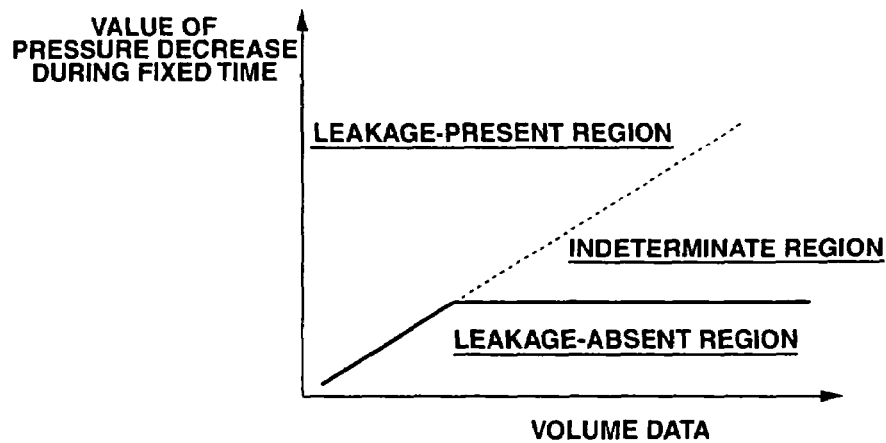
FIG. 17 is a diagram illustrating an example of regions for leakage presence/absence determination which is different from those of FIGS. 13, 14, 15, 16.
Figure 18:
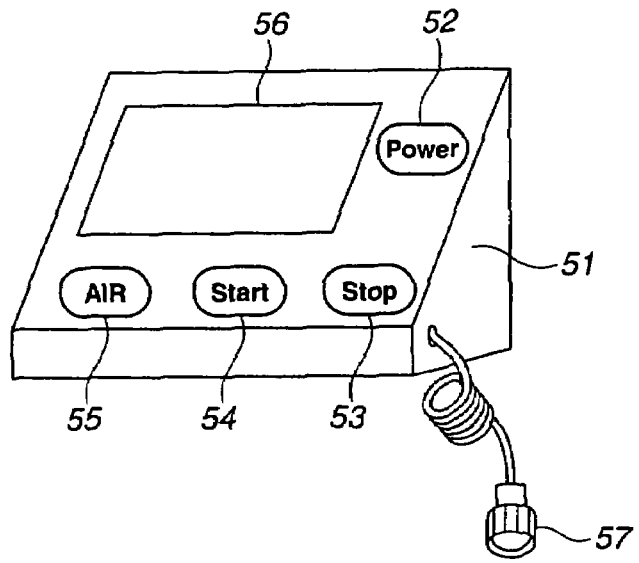
FIG. 18 is an exterior view of an endoscope leakage tester.
Figure 19:
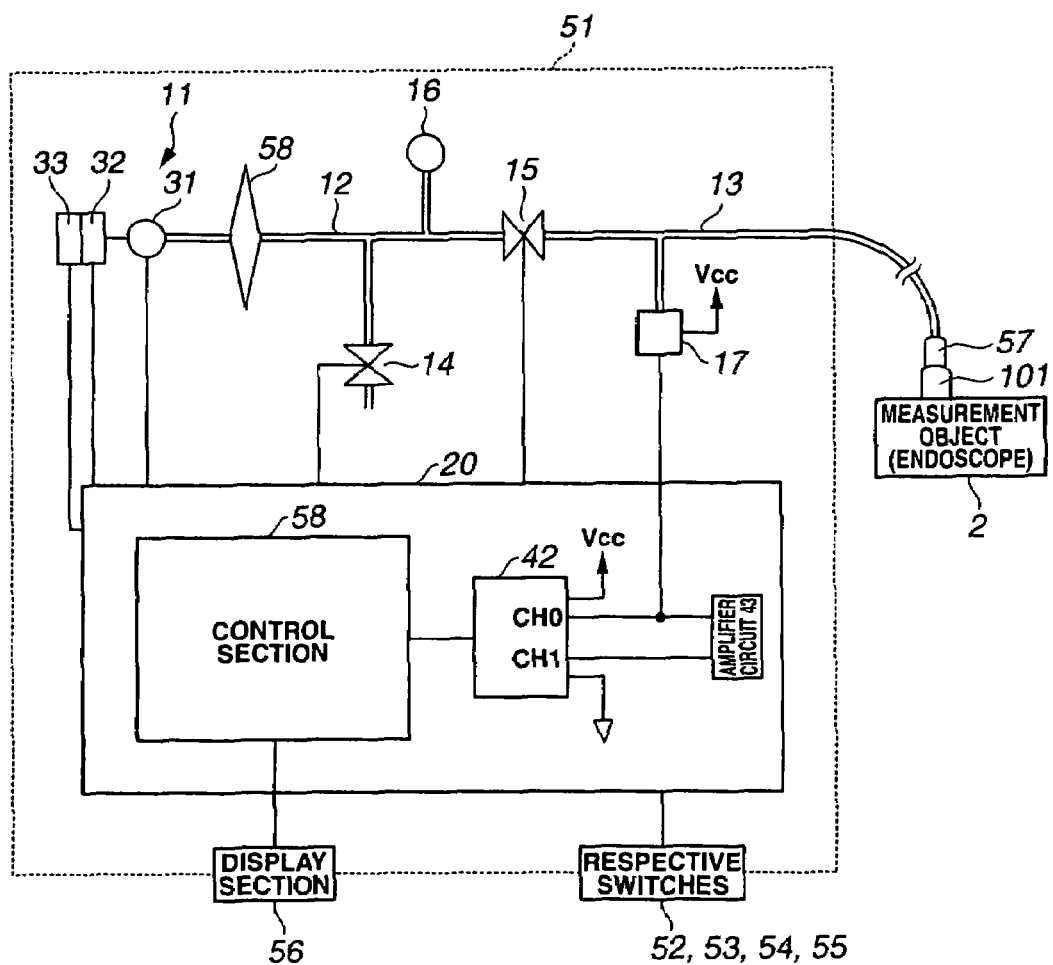
FIG. 19 is an overall block diagram of FIG. 18.

FIGS. 1 to 18 show an embodiment of the present invention. FIG. 1 is a block diagram showing the basic configuration of a leakage tester. FIG. 2 is a time chart illustrating how an air pump and on/off valves operate throughout the entire process. FIG. 3 is a diagram showing the transition of a pressure sensor output during the pressurization of an endoscope. FIG. 4 is a time chart illustrating how the air pump and the on/off valves operate during a volume measurement in the case where a leakage on the leakage tester side can be ignored. FIG. 5 is a diagram showing the transition of the pressure sensor output during the volume measurement. FIG. 6 is a time chart illustrating how the air pump and the on/off valves operate during the volume measurement in the case where the leakage on the leakage tester side cannot be ignored. FIG. 7 is a diagram showing the general configuration of the air pump. FIG. 8 is a diagram illustrating the transitions in pressure in an endoscope with no leak according to differences in pressurization time. FIG. 9 is a diagram illustrating an input/output characteristic of a common gauge pressure sensor. FIG. 10 is a conceptual diagram of a signal amplifier circuit. FIG. 11 is a diagram illustrating a method of performing signal amplification in a region that is subject to signal amplification. FIG. 12 is a diagram showing how V1, R1, and R2 are determined in FIG. 10. FIG. 13 is a diagram illustrating an example of regions for leakage presence/absence determination. FIG. 14 is a diagram illustrating an example of regions for leakage presence/absence determination which is different from that of FIG. 13. FIG. 15 is a diagram illustrating an example of regions for leakage presence/absence determination which is different from those of FIGS. 13, 14. FIG. 16 is a diagram illustrating an example of regions for leakage presence/absence determination which is different from those of FIGS. 13, 14, 15. FIG. 17 is a diagram illustrating an example of regions for leakage presence/absence determination which is different from those of FIGS. 13, 14, 15, 16. FIG. 18 is an exterior view of an endoscope leakage tester. FIG. 19 is an overall block diagram of FIG. 18.

First, the basic overall configuration of a leakage tester will be described with reference to FIG. 1. In FIG. 1, reference numeral 1 denotes a leakage tester, and the leakage tester 1 is mainly composed of an air pump 11, pipes 12, 13, on/off valves 14, 15, a relief valve 16, a gauge pressure sensor 17, and a control section 20.

The air pump 11 is a diaphragm type air pump, for example, which serves as pressurizing means and is connected to the on/off valve 15 via the pipe 12. Further, the on/off valve 15 is connected to the pipe 13.

Connected to the pipe 12 are the on/off valve 14 that is open to the atmosphere on one side and the relief valve 16. Further, an endoscope 2 as a measurement object, and the gauge pressure sensor 17 serving as pressure detecting means for measuring the internal pressure of the endoscope 2 are connected to the pipe 13.

With the above-described configuration, the control section 20 functions as volume estimating means and leak determination means and controls the air pump 11 and the on/off valves 14, 15 in accordance with a time chart shown in FIG. 2.

Hereinbelow, operation will be described with reference to the time chart of FIG. 2.

When a measuring operation for leak determination is started, first, a step of pressuring the inner portion of the endoscope 2 as the measurement object begins. In the pressurizing step, the control section 20 opens the on/off valve 15, closes the on/off valve 14, and drives the air pump 11. The pressure being pressurized is allowed to rise to, a fixed pressure determined by the relief valve 16. Then, once the inner portion of the endoscope 2 has been pressurized to the pressure determined by the relief valve 16, the control section 20 closes the on-off valve 15 and the process shifts to a balance step.

The balance step is intended to gain time until the distribution of the pressure inside the endoscope 2 and the pipe 13 becomes uniform. Although the operation states of the air pump 11 and of the on/off valve 14 in the balance step may be arbitrary, the air pump 11 is preferably stopped. Then, after the balance step has been finished, the process shifts to a measuring step. It should be noted that the state of the on/off valves remains unchanged during the shift from the balance step to the measuring step.

In the measuring step, the control section 20 monitors the output value of the gauge pressure sensor 17. The details of such monitoring will be described later. After the measuring step, the process shifts to an exhaust step of removing air inside the endoscope 2.

In the exhaust step, the control section 20 opens the on/off valves 14, 15, and stops the air pump 11 to thereby discharge the pressurized air in the endoscope 2 to the atmosphere. The measuring operation is complete when the exhaust step is ended.

With regard to the exhaust step, if the connection between the pipe 13 and the endoscope 2 does not include any check valve and disconnection allows the inner portions of the endoscope 2 and of the pipe 13 of the leakage tester 1 to be released to the atmosphere, then the exhaust step may be replaced with disconnection of this part. In that case, the on/off valve 14 for exhaust may be omitted from the configuration shown in FIG. 1. In this case, the on/off valve 15 is made to remain open when the measuring operation is not being performed (including standby state and power off state).

Next, description will be made on the measurement of the internal volume of the endoscope 2 which is normally executed in the above-described pressurizing step.

When there is a leakage of a fixed amount (unit: ml/min) from a sealed container, including those other than an endoscope, the change in the internal pressure of the container (per fixed period of time) varies according to the volume of the container used. The smaller the volume, the larger the decrease in pressure per fixed period of time. Since an object of the present application is to prevent a failure in an endoscope, a leakage tester with higher accuracy can be realized by detecting a hole of a fixed size, that is, leakage of a fixed amount or more.

Here, although the volume can be inferred from the way the pressure increases if the measurement object is a simple container, an endoscope is a rather complex device that is elongate with various components provided therein. Further, the connection port for pressurizing the inner portion of the endoscope is provided at the terminal end of the endoscope. Accordingly, the leakage tester 1 shown in FIG. 1 has an elongated configuration, with the pressure sensor, the pressurization pump, and the like being connected to the terminal end of a pipe that offers resistance to air.

Accordingly, when, with the configuration shown in FIG. 1, the endoscope 2 is connected, the output of the gauge pressure sensor 17 becomes non-linear as shown in, for example, FIG. 3. This phenomenon peculiar to the endoscope 2 makes it a rather complex process to infer the volume from the way the pressure increases as seen by the gauge pressure sensor 17. In view of this, instead of performing the measurement in the transient state such as during the starting phase of the pressurization, the pressurization is temporarily stopped, and the pressure measurement using the gauge pressure sensor 17 is performed after the pressures in the endoscope 2 and in the pipe 13 including the gauge pressure sensor 17 become substantially uniform, thereby estimating the volume of the measurement object including the endoscope 2.

First, if leaks from the pipe 12, air pump 11, relief valve 16, and on/off valve 14 can be ignored, the control section 20 performs the operation as shown in FIG. 4. That is, after the start of pressurization, the pressurization is carried out for a time period TA, after which the air pump 11 is stopped for a time period TB. The transition of the output of the gauge pressure sensor 17 at this time is as shown in FIG. 5. The value at the time when the pressure becomes substantially constant during the time period TB is stored as the volume data of the endoscope 2, and after the time period TB has elapsed, the air pump 11 is driven again to resume the pressurization.

Conversely, when leaks from the pipe 12, air pump 11, relief valve 16, and on/off valve 14 cannot be ignored, the control section 20 closes the on/off valve 15 to thereby realize the measurement. In this case, the control section 20 performs the operation as shown in FIG. 6. That is, after the pressurization is carried out for the time period TA, the on/off valve 15 is closed for the time period TB. The operation conditions of the air pump 11 and on/off valve 14 during the time period TB may be arbitrary. Then, after the time period TB has elapsed, the on/off valve 15 is opened to resume the pressurization.

Now, the time periods TA and TB mentioned above will be described.

The time period TA may be any time period as long as it satisfies the condition under which the amount of air put into the endoscope 2 becomes a fixed value. Most simply, it may be set as a fixed period of time. It should be noted, however, that considering the characteristics of the air pump 11 and of the system, that is, degradation of the motor of the air pump 11, variations in power source voltage, and the like, the time period TA may be set as the time it has taken the RPM of the pump head to reach a fixed RPM.

Here, in the case where the air pump 11 is that of a diaphragm type, the amount of air sucked by the pump, that is, the amount of air pumped out from the pump is determined on the basis of how many times the piston of the diaphragm pump head has reciprocated. Accordingly, the rotation of the motor that drives the pump head is counted, and the pressurization is stopped when the motor has rotated by a fixed amount. For example, as shown in FIG. 7, the air pump 11 is constructed by attaching a pulse generator 33 to a motor 32 that drives a pump head 31. Further, after the start of the pressurization, the control section 20 counts the output pulse of the pulse generator 33 and causes the air pump 11 to stop when the counted value has reached a fixed value.

Further, the time period TB may be a fixed period of time. Although the exact time period varies according to the kind, that is, the size and length of the endoscope 2, it has been found through an experiment that even in the case where the endoscope 2 used has a large volume, stoppage for 1.5 to 2 seconds suffices to stabilize the pressure to a degree that will not affect the measurement results. During this time period, the control section 20 reads the output of the gauge pressure sensor 17 and stores it as the volume data of the endoscope 2 as the measurement object.

Next, the pressurization time period in the pressurizing step will be described. As described above, the endoscope 2 is elongated with air resistance present therein; accordingly, if the pressurization is stopped immediately after the pressure as seen by the gauge pressure sensor 17 has reached the pressure that is determined by the relief valve 16, a decrease in pressure occurs even in the case of the endoscope 2 with no leak due to the internal pressure trying to become constant. This phenomenon must be avoided because it makes it impossible to determine whether the pressure decrease occurring during the measurement is one due to leakage or one due to insufficient pressurization.

A better illustration in this regard is provided by a diagram as shown in FIG. 8. FIG. 8 illustrates the transitions in pressure according to differences in pressurization time using the endoscope with no leak. By continuing the pressurization until a point B instead of stopping it at a point A, and by continuing the pressurization until a point C instead of stopping it at the point B, a pressure decrease resulting from the above-mentioned phenomenon becomes less liable to occur because the entire inner portion of the endoscope 2 is subjected to uniform pressurization.

Although also depending on the capacity of the air pump 11, it has been found through an experiment that when using a DC motor-driven diaphragm pump with an air supply rate of 1.4 L/min at a lock pressure of 1 kg/cm$^2$, 0.4 kg/cm$^2$, if the set pressure is within the range of 0.2 to 0.5 kg/cm$^2$, the above phenomenon will be suppressed to an extent hardly affecting the leak measurement in 40 to 90 seconds.

Next, the monitoring circuit will be described.

When a gauge pressure system is adopted, a variation in sensor output due to a decrease in pressure become small. Thus, the influence of power source voltage variations of the sensing circuit, sensor offset errors or temperature characteristics, or the like cannot be ignored. In general, a piezo-type pressure sensor exhibits the characteristic as shown in FIG. 9, although this may move upwards or downwards or to the right or left, its inclination itself is stable in most cases (generally at about ±1%). Accordingly, with the gauge pressure output value at arbitrary time during the balance step or at the start of the measurement taken as the initial value, by determining the pressure decrease value based solely on the amount of change from the initial value per unit time, the influence of vertical offset can be ignored because the inclination is stable.

Further, the control section 20 is generally adapted to perform digital conversion on the sensor output using an AD converter. In this regard, by inputting the power source of the sensor to a reference voltage Vref of the AD converter, even when the sensor output fluctuates due to a variation in voltage, the reference voltage of the AD converter also changes simultaneously, whereby the obtained digital value becomes stable. The variation in voltage can be thus ignored.

It should be noted that it is common to use an AD converter and directly input the output of the gauge pressure sensor 17 to the AD converter to thereby detect the pressure value. However, if the resolution of the AD converter is low, the detection accuracy may decrease due to conversion errors in performing digital conversion with respect to minute pressure changes. Accordingly, there may be used a converter with a high resolution (12 bit or more), or an AD converter with a low resolution of 8 to 10 bit may be used in the circuit configuration as shown in FIG. 10.

Now, a brief description will be made on a signal amplifier circuit of the gauge pressure sensor 17 with reference to FIG. 10. As described above, the power source Vcc of the gauge pressure sensor 17 is input to the reference voltage Vref of the AD converter 42, thus effecting connection in a manner allowing the influence of voltage variations to be ignored. Further, the output (voltage output type) of the gauge pressure sensor 17 is subjected to analog-signal processing by an amplifier circuit mainly composed of an OP amplifier 41, and the resultant output is input to the AD converter 42.

The amplifier circuit mainly composed of the OP amplifier 41 has an extremely simple configuration, and performs signal conversion as represented by the following expression.

$$Vout=(R2 \cdot (Vin-V1))/R1$$

Here, Vin represents the output of the gauge pressure sensor 17, Vout represents the output of the amplifier circuit, and V1 represents a reference voltage that can be adjusted and fixed by a trimmer; each of those is expressed in unit of volt (V).

As can be appreciated from the above expression, when the voltage becomes $\beta$ times, Vin and V1 also become $\beta$ times, so Vout also becomes $\beta$ times of that before the change. This allows the variation in power source voltage, including V1, to be ignored.

FIG. 11 is a conceptual diagram of the operation performed in the circuit of FIG. 10. That is, the inside of the endoscope 2 is pressurized through normal pressurization to the pressure determined by the relief valve 16; when there is a leak after the closure of the on/off valve 15, then the pressure decreases thereafter. By magnifying the decrease in pressure and inputting it to the AD converter, the above-described errors in digital conversion can be absorbed. In view of this, as shown in FIG. 11, conversion is performed with respect to only the pressure region that is desired to be measured, using the full scale of the AD converter.

It should be noted in this regard that a reference value for determining the presence/absence of leakage is separately determined; with respect to the pressure decrease by the reference leak, a region that takes the vertical margin into account may be magnified for input to the AD converter.

For easier understanding, referring to FIG. 12, description will be made on how V1, R1, and R2 in FIG. 10 are determined.

First, a case is considered in which the pressurization pressure is 0.4 kg/cm², for example, and the value $\beta$ in FIG. 12 is set to 0.3 kg/cm² by taking the pressure decrease and the margin into account, with a value $\gamma$ in the same drawing being set to 0.45 kg/cm² on the basis of the pressurization errors and the margin. In this case, since the value $\alpha$ can be immediately found ($\alpha=\gamma-\beta$), a sensor output variation value $\alpha'$ for $\alpha$ is calculated. Then, R1, R2 are calculated so that ($\alpha' \cdot$R2)/R1=Vcc (AD converter reference voltage).

Next, as for V1, since $\beta$=0.3 kg/cm², without using a trimmer, the sensor output (V) is calculated through an inverse operation, thus adjusting it so as to conform to the resultant value. Alternatively, while performing a voltage measurement using a trimmer, the resultant value may be used, or a method of adjusting a trimmer so that V1=Vin while actually applying a pressure of 0.3 kg/cm² may be employed.

In the case of this example, if a gauge pressure sensor with a full scale of 0.5 kg/cm² is used, a region corresponding to 30% of the full scale is subjected to full scale conversion with the AD converter, so the resultant effect is the same as using an AD converter having a resolution approximately 3.3 bit more than that of the AD converter used.

Since the output of a gauge pressure sensor with amplifier is not 0 to Vcc but a vertical offset (about 0.5 V) is often provided therefore, in the case of this example, an effect of further improvement in resolution can be attained. In this case, roughly speaking, an 8 bit AD converter can be converted into one equivalent to a 12 bit AD converter.

Next, a method of determining the presence/absence of leakage will be described.

Since the amount of leakage depends on the size of a hole, it is preferable that a fixed amount of leakage serves as the determination criterion. When the leakage (ml/min) is constant, the change in pressure is simply proportional to 1/V (V: volume). Further, as for the data due to the volume measurement as described above, with the pressure increase value taken as volume data, it is proportional to 1/V (V: volume). Thus, the relationship between the volume measurement data and the pressure decrease data due to leakage is proportional.

While those relationships are obtained through simple calculation while ignoring the temperature rise due to pressurization, it has been found that the characteristic as shown in FIG. 13 can be obtained with the actual endoscope. Accordingly, as shown in FIG. 13, it is determined that there is leakage for the region above the line representing this characteristic, and that there is no leakage for the region below the same.

Further, as a case peculiar to an endoscope, when measurement was performed on an endoscope with no leak, it was found that the pressure decrease values per fixed period of time with respect to volume data are distributed in the leakage-absent region shown in FIG. 14.

Accordingly, in order to enhance the detection accuracy and to prevent an erroneous detection in the case of an endoscope with small volume data (that is, an endoscope having a large volume), the solid line in FIG. 14 may serve as the determination criterion. Referring to the examples of the settings shown in FIG. 13 and FIG. 14, a point Vol in FIG. 14 may represent the case where the volume is 400 to 800 ml, with an amount of 1 to 10 ml/min taken as the reference leak amount. At this time, the pressurization pressure is set to be within the range of 0.2 to 0.5 kg/cm².

Of course, when the criterion for determining the presence/absence of leakage is set as, for example, 10 ml, as shown in FIG. 15, a fixed decrease in pressure may serve as the determination criterion.

Further, rather than determining only the presence/absence of leakage, as shown in FIG. 16, an indeterminate region may be provided as a region for which a definite determination is difficult to make. In the case of FIG. 16, for example, the determination criterion for the leakage-present region/indeterminate region is set as 4 ml/min, whereas the determination criterion for the indeterminate region/no-leakage region is set as 2 ml/min.

Further, when it is desired to set an indeterminate region for the determination map as shown in FIG. 14, the indeterminate region may be set as in, for example, FIG. 17. That is, the indeterminate region may be set, in the case where the volume data value is relatively large, between the portion above the no-leakage region and the leakage-present region.

Here, if the determination result falls within the indeterminate region, it is preferable to urge the user to perform the conventional water immersion bubble leak test by visual checking. This is because this leak test method ensures higher accuracy in detecting leakage.

Hereinbelow, an automatic endoscope leakage tester having the above-described functions will be described more specifically.

FIG. 18 is an exterior view of the endoscope leakage tester. A main body 51 thereof is provided with a power switch 52, a stop switch 53, a start switch 54, an air supply switch 55, a display section 56, and a scope connection connector 57.

As shown in FIG. 19, the main configuration of the endoscope leakage tester is based on the configuration shown in FIG. 1 described above. It should be noted that in FIG. 19, reference numeral 58 denotes an air filter, which is disposed downstream of the discharge port of the air pump 11 for the purpose of dust-proof protection.

Further, the control section 20 has a built-in circuit based on the arrangement of FIG. 10 described above and composed of the gauge pressure sensor 17, the amplifier circuit 43, and the AD converter 42.

Further, in addition to the circuit shown in FIG. 10, the output of the gauge pressure sensor 17 is directly input to another input port of the AD converter 42. This configuration makes it possible for a single gauge pressure sensor 17 to perform both volume measurement and detection of a pressure decrease due to leakage.

The AD converter 42 is connected to a control section 58 provided inside the control section 20. Further, the display section 56, and the respective switches 52 to 55 are connected to the control section 20. Further, connected to the scope connection connector 57 is a leak detection connector 101 connected to the inner space of the endoscope 2.

Further, the air supply switch 55 is provided for the purpose of carrying out the commonly employed leak test method, which involves immersion into water followed by visual checking of the generated bubbles, in the case where the determination result indicates the presence of leakage or is indeterminate. The pressurization pressure at this time may be the pressure determined by the relief valve 16; when intending to make the pressure lower, the output of the gauge pressure sensor 17 may be read by CH0 of the AD converter 42, with the motor 32 that drives the pump head 31 of the air pump 11 being driven so as to attain an arbitrary pressure. This allows the leakage to be checked again, and, further, enables the leakage tester of the present invention to be used for the measurement object other than the endoscope 2 that is subject to a leak test relying on visual checking of bubbles.

The endoscope leakage tester operates as follows. The operations of the respective on/off valves 14, 15 and of the air pump 11 are as described above.

1) Pressurizing Step

After pressurization has been started, the volume is measured as described above. At this time, the output of the gauge pressure sensor 17 is input to the CH0 of the AD converter 42. If the pressurization is not complete at this point, it is presumed that there is a marked leakage from the endoscope 2 or that there is a defect in the leakage tester (pipe disconnections, pump inactivation, or the like), so the operation is stopped and a warning is displayed to that effect.

Then, the pressurization is sustained even after the predetermined pressure as determined by the relief valve 16 is reached within the predetermined time, and the process shifts to the next step after, for example, 40 to 90 seconds has elapsed after the start of pressurization. It should be noted that in the pressurizing step, the volume data of the endoscope 2 is previously obtained as described above.

2) Balance Step

The process waits for the pressure in the endoscope 2 to become uniform. During this step as well, the pressure in the endoscope 2 is monitored to check for the presence/absence of an abrupt pressure decrease due to the presence of a relatively large leakage. This checking is performed by monitoring the value of either one or both of the CH0, to which the output of the gauge pressure sensor 17 is input as it is, and CH1 to which it is input via the amplifier circuit 43.

If there is an abrupt pressure decrease, it is determined that there is leakage and the process shifts to the exhaust step. Subsequently, the operation is stopped and a display is provided to show the results.

3) Measuring Step

In the measuring step, first, the output data CH1 of the gauge pressure sensor 17 via the amplifier circuit 43 is monitored. Since the variation in pressure in the endoscope 2 is not linear, measurement is carried out for a fixed period of time, and the pressure decrease value is obtained from the resultant average value. On the basis of this result and the volume data obtained in the pressurizing step, a determination result is obtained using the above-described determination criteria. After the measurement for leak determination, the process shifts to the next step.

It should be noted that a determination criterion is preferably provided even for a pressure decrease value per each unit time. For better understanding in this regard, it is to be noted that the determination criterion for the presence/absence of leakage in the balance step is detection of a relatively large hole; on the other hand, the criterion for determination after the elapse of the predetermined period of time in this measuring step is detection of a small hole. Accordingly, it is also possible to make a quick determination with respect to a hole of a size ranging from relatively large to small (for the sake of convenience, such a hole is called an intermediate hole). That is, the pressure decrease value per unit time to be used for making a determination with respect to an intermediate hole is previously set. Specifically, the easiest method would be to obtain the pressure decrease value per unit time from the reference value for a small hole, and use the value obtained by adding an arbitrary number thereto as the determination criterion (per unit time). When there is a decrease in excess of the reference pressure decrease value per unit time, the presence of leakage is determined at that point, and the process shifts to the next step.

4) Exhaust Step

After the pressurized air has exhausted for a predetermined time, the process returns to a standby state.

It should be noted that according to the present invention, the components such as the air pump 11, the on/off valves 14, 15, the relief valve 16, and the gauge pressure sensor 17 are not limited to those illustrated in the drawings as long as the components used provide the required functions.

According to the configuration described above, a leak test can be easily carried out, and miniaturization and low cost can be realized in comparison to conventional products because there is no need to provide a separate flow meter.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A leakage tester, comprising:
    a pressurizing apparatus for pressurizing a measurement object by introducing gas into the measurement object;
    a pressurization control section for controlling the pressurizing operation by the pressurizing apparatus such that the pressuring apparatus performs a first pressurizing operation to stop pressurizing before reaching a predetermined pressure after starting pressurizing and a second pressurizing operation to stop pressurizing after pressurized until reaching the predetermined pressure after the first pressurizing operation;
    a pressure detecting section for detecting the pressure in the measurement object, the pressure detecting section detecting at least the pressure value in the measurement object when the first pressurizing operation is stopped and the value of pressure change in the measurement object after the second pressurizing operation is stopped;
    a volume estimating section for estimating the volume of the measurement object based on the pressurizing amount of the first pressurizing operation and the pressure value when the pressurizing operation is stopped; and
    a leak determination section for determining the leakage state of the measurement object based on the pressure change information obtained in accordance with the volume of the measurement object estimated by the volume estimating section and the amount of pressure change detected by the pressure detecting section after the second pressurizing operation is stopped.

2. The leakage tester according to claim 1, wherein the pressurization control section starts the second pressurizing operation after elapse of a preset period of time after the first pressurizing operation is ended.

3. The leakage tester according to claim 2, wherein the pressure detecting section measures the pressure value of the measurement object after elapse of a preset period of time after the first pressurizing operation is ended and before the second pressurizing operation is started, and measures the amount of pressure change in the measurement object after elapse of a preset period of time after the second pressurizing operation is ended.

4. The leakage tester according to claim 1, wherein the pressurizing apparatus is an air pump such as of a diaphragm type.

5. The leakage tester according to claim 4, further comprising:
    an rpm detecting apparatus for detecting an rpm of a pump head mounted in the air pump, wherein the pressurization control section stops the first pressurizing operation in response to the rpm of the pump head detected by the rpm detecting apparatus.

6. The leakage tester according to claim 1, wherein the pressurization control section stops the first pressurizing operation after elapse of a preset period of time after the first pressurizing operation is started.

7. The leakage tester according to claim 1, wherein the measurement object is the endoscope having an elongate insertion portion, and in case the pressurization pressure of the pressurizing apparatus is set to 0.2 to 0.5 kg/cm$^2$, the time from starting the first pressurizing operation to ending the second pressurizing operation controlled by the pressurization control section is 40 to 90 seconds.

8. The leakage tester according to claim 1, wherein the measurement object is an endoscope having an elongate insertion portion, and in case the pressurization pressure of the pressurizing apparatus is set to 0.2 to 0.5 kg/cm$^2$, the leak determination section sets whether the amount of air leaking through a leakage hole is in the range of 1 to 10 ml/min as a criterion for determining presence/absence of leakage.

9. The leakage tester according to claim 1, wherein the leak determination section determines the state of presence of leakage if the amount of pressure decrease is more than a predetermined amount after the second pressurizing operation is ended.

10. The leakage tester according to claim 1, wherein the leak determination section determines the state of presence of leakage if the amount of pressure decrease per unit time is more than a predetermined amount when the pressure detecting section detects the amount of pressure change in the measurement object after the second pressurizing operation is ended.

11. The leakage tester according to claim 1, wherein, in case the measurement object is an endoscope having an elongate insertion portion, the leak determination section warns the user if the volume estimated by the volume estimating section is of a value not within a predetermined range.

* * * * *